(12) United States Patent
Butlin et al.

(10) Patent No.: US 7,410,768 B2
(45) Date of Patent: Aug. 12, 2008

(54) TEST METHODS AND DEVICES

(75) Inventors: Lorraine D. Butlin, Bedford (GB); John Coley, Bedford (GB); Stephen J. Eida, Bedford (GB); Mohamed M. Gani, Bedford (GB)

(73) Assignee: Inverness Medical Switzerland GmbH, Zug (CH)

( * ) Notice: Subject to any disclaimer, the term of this patent is extended or adjusted under 35 U.S.C. 154(b) by 50 days.

(21) Appl. No.: 09/824,587

(22) Filed: Apr. 3, 2001

(65) Prior Publication Data

US 2002/0045273 A1    Apr. 18, 2002

(30) Foreign Application Priority Data

Apr. 3, 2000    (EP)    ................................ 00302811

(51) Int. Cl.
*G01N 33/53*    (2006.01)

(52) U.S. Cl. ...................... 435/7.1; 435/7.9; 435/7.94; 435/960; 436/501; 436/510; 436/547; 436/548; 436/814; 436/817; 436/818; 436/815; 436/806

(58) Field of Classification Search ................ 435/7.1, 435/7.9, 7.94, 960; 436/501, 510, 547, 548, 436/817, 818, 814, 815, 806
See application file for complete search history.

(56) References Cited

U.S. PATENT DOCUMENTS 4,900,662 A * 2/1990 Shah et al.

FOREIGN PATENT DOCUMENTS

EP    0736771    * 10/1996

OTHER PUBLICATIONS

Creus et al., Clinical Endocrinology. Feb. 1996. vol. 44, No. 2, pp. 181-189.*
Niccoli et al., Eur. J. Clin. Chem. Clin. Biochem. 1996. 34:741-748.*
Alfthan et al., Molecular and Cellular Endocrinology. 1996. 125:107-120.*
Matikainen et al., Journal of Clinical Endocrinology and Metabolism. 1992. 75(3):820-825.*

* cited by examiner

*Primary Examiner*—Bao-Thuy L Nguyen
(74) *Attorney, Agent, or Firm*—Beth E. Arnold; Foley Hoag LLP

(57)    ABSTRACT

A method and test device for differentiating between states of an analyte that can exist in different forms, such as follicle stimulating hormone (FSH). The method or test device uses a pair of specific binding agents, especially monoclonal antibodies, in two assays for the same analyte. The assays, applied to contemporaneous samples, differ from one another in format, one being a two step assay and the other being one step. A novel pair of anti-FSH monoclonal antibodies that can be used together in two such assays to differentiate pre-menopausal and post-menopausal FSH samples is disclosed.

11 Claims, No Drawings

TEST METHODS AND DEVICES

FIELD OF THE INVENTION

This invention relates to test methods and devices, and more particularly to methods for differentiating between states of an analyte that exists as various forms, e.g. isoforms.

BACKGROUND TO THE INVENTION

Tests are available, or have been proposed, which purport to provide clinically significant information about hormonal levels of relevance to the menopause. The principal hormone of interest is follicle stimulating hormone (FSH). The postmenopausal state has been associated with a rise in the level of circulating FSH. For this purpose tests have been developed to detect the level of FSH in body fluid samples such as blood and urine. These tests are intended to detect "total" FSH, in the sense that they do not discriminate between different isoforms of FSH.

These known tests are used by clinicians in recommending and monitoring hormone replacement therapy (HRT). As the menopause is also associated with a drop in the level of circulating estrogen metabolites, HRT normally involves administration of estrogen in order to reduce this deficit and counteract symptoms associated with the menopause.

Although it is known that FSH exists in various forms, the clinical significance of these in relation to conditions such as the menopause is poorly understood. The differing forms may be isoforms or glycoforms. However, the existence of these differing forms calls into question the soundness of "total" FSH tests as a basis for good clinical diagnosis.

There is a need for an improved method of monitoring gonadotrophin hormones, especially FSH, to provide more reliable diagnosis of menopausal conditions and to facilitate the prescription and regulation of HRT.

More generally, there is a need for a method for differentiating between states of an analyte that exists as a plurality of forms, especially when the nature and/or relative amounts of such forms present in a sample of the analyte may be of clinical significance. The forms may differ from one another in either physical characteristics (e.g. "isoforms" separable by charge) or chemical characteristics (e.g. "glycoforms" in the case of FSH or similar molecules), or indeed both.

GENERAL DESCRIPTION OF THE INVENTION

The invention provides a method for differentiating between two states of an analyte that exists in a plurality of forms, which states differ from one another in the nature and/or amount of one or more forms present therein, in which method a sample, or contemporaneous samples, containing the analyte are: (a) subjected to a two step specific binding assay utilising a first binding agent specific for the analyte and a labelled second binding agent specific for the analyte to provide a first test signal proportional to the amount of analyte present in the sample, wherein, in a first step of the two step assay, the analyte is contacted with the first binding agent to form a first binding agent/analyte complex, and in a second step of the two step assay, the first binding agent/analyte complex is contacted with the labelled second binding agent, to form a first binding agent/analyte/second biding agent complex; and (b) said sample or samples are also subjected to a one step-specific binding assay utilising the same pair of analyte-specific binding agents, in which one step assay the analyte is contacted with both first and second binding agents substantially simultaneously, to form the first binding agent/analyte/second binding agent complex, to provide a second test signal proportional to the amount of analyte present in the test sample; and wherein at least one member of said pair of binding agents having a different specificity for each of said two states of said analyte, and the first test signal is compared to the second test signal.

The one step assay involves contacting the analyte with the first and second binding agents "substantially simultaneously". A short delay between the analyte coming into contact with one or other of the binding agents, of the matter of say 1-2 minutes (at room temperature) will not normally be critical. What is important is that the analyte does not have an opportunity to reach equilibrium, with respect to its binding to one of the binding agents, before coming into contact with the other binding agent. Clearly this depends on the kinetics of the reaction, which in turn depend on the identities of the analyte and binding partners involved, and the temperature. Accordingly the term "substantially simultaneously" as used herein should be construed as meaning that both binding agents should be contacted with the sample before 60%, (preferably before 70%, more preferably before 80%, and most preferably before 90%) of the analyte in the sample has become complexed with one of the binding agents.

Preferably, each member of said pair of binding agents has a different specificity for each of said two states of said analyte.

Desirably the specific binding agents comprise an antigen binding site of an immunoglobulin. One or both specific binding agents may advantageously be an antibody (e.g. an IgG or IgA molecule), especially a monoclonal antibody, or comprise any antigen binding portion thereof, such as Fv, Fab, scFv, bispecific antibodies, "diabodies" and the like, all of which are well known to those skilled in the art.

Conveniently, a combined test result may be expressed as a ratio of the two test signals. Optionally, the ratio of the two test signals is compared to a standard ratio for one or other of the two states to determine in which state the sample analyte exists.

The method of the invention is especially applicable when the analyte is a gonadotrophin, such as FSH.

It will be apparent to those skilled in the art that the first and second binding agents must not bind to identical sites on the analyte, so that a complex (the "first binding agent/analyte/second binding agent complex") may be formed in which both first and second binding agents are simultaneously bound to the analyte, in a "sandwich" type assay, well known to those skilled in the art.

In the two step assay, it is generally preferred that following performance of the first step, the first binding agent/analyte complex is separated from any excess analyte present in the sample prior to contacting the complex with the labelled second binding agent, so as to prevent binding of the second binding agent to any uncomplexed analyte. This separation may be achieved in any suitable manner. For example, in one embodiment, in the first step of the assay the sample is incubated with a solid phase on which is immobilised the first binding agent, and thereafter following a washing step to remove unbound analyte, the solid phase is incubated with the labelled second binding agent.

In the one step assay the sample may be simultaneously incubated with a solid phase on which the first binding agent is immobilised and with the labelled binding agent in solution or suspension. Preferably, however in the one step assay the sample is simultaneously incubated with the first binding agent in solution or suspension and with the labelled second binding agent in solution or suspension, and the first binding agent is thereafter immobilised on a solid phase.

The solid phase may be any suitable solid support, such as a microtitre place, a membrane, a latex bead or the like.

As one option, immobilisation of the first binding agent on the solid phase is effected through a specific binding reaction, such as an avidin-biotin interaction, but numerous other specific interactions are known and could be employed (e.g. coating the solid phase with an Ig-specific antibody).

It will be apparent from the foregoing that it is an essential feature of the invention that at least one of the specific binding agents is labelled, to allow at least qualitative (preferably quantitative) detection of the formation of the first binding agent/analyte/second binding agent complex. Any conventional labelling method may be used (e.g. an enzyme label, fluorescent label, radio-label), but preferred labels include direct particulate labels, such as a gold sol or a coloured latex particle.

Generally it is the second binding agent which is labelled. However, it is possible that the first binding agent may also be labelled (for example, with biotin or some other label, to facilitate immobilisation on a solid phase, as outlined above). In such circumstances, it is desirable that the label on the first binding agent should not interact in any way with the detection system used in the assay to detect the label on the second binding agent. Conveniently this is arranged by ensuring that any label provided on the first binding agent is different to the label provided on the second biding agent.

In particular the invention provides a method of monitoring the hormonal status of an individual human female subject in which the contemporaneous tests are conducted repeatedly, i.e. at regular intervals such as every few weeks, to determine whether the gonadotrophin level and/or its character are changing in a manner which indicates entry into or departure from a menopausal state.

Another embodiment of the invention is an assay device for testing a body fluid sample obtained from a human subject (preferably a female), the device having a first analyte-responsive (preferably gonadotrophin-responsive) signal-producing means that provides a readable signal by means of a two step assay as described herein, and a second analyte-responsive (preferably gonadotrophin-responsive) signal-producing means that provides a readable signal by means of a one step assay as described herein. Typically the assay signals will differ depending on whether the sample is derived from a pre-menopausal or post-menopausal subject.

In a further aspect, the invention provides a test kit for testing a body fluid sample obtained from a human subject (preferably a female), the kit comprising a first analyte-responsive (preferably gonadotrophin-responsive) signal-producing means that provides a readable signal by means of a two step assay as described herein, and a second analyte-responsive (preferably gonadotrophin-responsive) signal-producing means that provides a readable signal by means of a one step assay as described herein, together with instructions for use in the method of the invention. In one embodiment, the first and second analyte-responsive signal-producing means are provided on a single test device. In an alternative embodiment, the first and second signal-producing means are provided on respective first and second test devices.

Each readable signal can be caused by the binding in a detection zone of a specific binding agent labelled with a direct particulate label, such as a gold sol or coloured latex particle. Alternatively, other signal-producing labels can be used, for example enzyme labels, fluorescent labels or radio-labels.

The contemporaneous tests of the invention can be conducted repeatedly, generally at an interval of at least a week, to monitor the effectiveness of a course of HRT.

Although FSH is the preferred analyte for use in accordance with the invention, other members of the gonadotrophin family can be used. These include human chorionic gonadotrophin (hCG), luteinizing hormone (LH) and thyroid stimulating hormone (TSH). All of these gonadotrophins are glycopeptides. Their principal structure comprises two peptide chains. One peptide chain, known as the alpha chain, is common to all members of the family. The other peptide change, known as the beta chain, differs in each molecule. In addition, each molecule contains glycoprotein side chains. The detailed structure of these molecules is not completely understood. However it is believed that variations in the composition of the glycoprotein side chains give rise to different forms ("glycoforms") of each molecule. Those skilled in the art will appreciate that differences in the chemical properties of the glycoprotein side chains may also influence the physical properties (e.g. charge) of the overall molecule, such that different glycoforms may also constitute different isoforms. Thus, in the case of FSH for example, on present scientific knowledge it is believed that the alpha and beta peptide chains are the same in all FSH forms, but subtle differences occur in the glycoprotein side chains. It is believed that the relative proportions of the forms of FSH existing in the menopause state are different from those in the pre-menopause state.

Prior to this invention it was not appreciated that a combination of specific binding assays could be developed which would differentiate between the FSH forms, to an extent sufficient to enable worthwhile detection of a menopausal state to be achieved, or that by using two different formats together an assay could provide enhanced differentiation.

In a preferred embodiment of the invention both assays are of the sandwich format. Each assay therefore requires two specific binding agents (e.g. antibodies), one preferably directed against the alpha chain and the other preferably against the beta chain of the FSH molecule. The two antibodies must be different. In a preferred embodiment the invention uses two sandwich-format immunoassays for FSH, one a two step assay and the other a one step assay, in which the antibodies are directed against the alpha and beta peptide chains of the molecule, but are exhibiting differences in specificity for certain forms of FSH caused by subtle changes in the glycoprotein side chains.

Antibody pairs appropriate for use in the invention can be identified by screening a range of anti-FSH antibody pairs against FSH samples obtained from pre-menopausal and post menopausal women.

In order to provide a source of antibodies from which to select an antibody pair which under the circumstances of the method of the invention differentiate between analyte forms, it is desirable, although not essential, to raise a panel of antibodies against the analyte forms in question. This can be done by routine hybridoma technology. Alternatively, immunoglobulin-producing bacteriophage libraries may be screened.

A particular aspect of the invention in relation to its application to the analysis of FSH samples is a pair of novel anti-FSH monoclonal antibodies that distinguish between pre-menopausal and post-menopausal FSH samples. Two murine hybridoma cell lines each expressing one of these novel monoclonal antibodies have been deposited in accordance with the provisions of the Budapest Treaty 1977 in the European Collection of Cell Cultures (ECACC, Centre for Applied Microbiology & Research, Salisbury, Wiltshire SP4 0JG, UK) as follows:

a) Balb/c murine hybridoma clone "4813.2" expressing an anti-beta-FSH monoclonal antibody: ECACC 00032004; and c) Balb/c murine hybridoma clone "4882.1" expressing an anti-alpha-FSH monoclonal antibody: ECACC 00032005, (both deposited on 20 Mar. 2000).

The invention includes the use of either or both of the anti-FSH monoclonal antibodies as expressed by these deposited cell lines, in a method or analytical test device as set forth herein.

The methods of the invention may be performed using any suitable sample, generally samples of body fluid from a subject. The body fluid may be any suitable body fluid, such as blood, serum, plasma, sweat, tears, crevicular fluid and the like. Most conveniently the sample is a sample of urine, which can easily be obtained without performing any invasive procedure.

In practice the two assays should be performed on the same clinical sample, sub-divided if necessary, or on two samples obtained from the same individual subject at more or less the same time (i.e. on the same day, and preferably in the same hour), so that the two assays give results that can fairly be compared with each other. It is in this sense that we regard the assays as being contemporaneous. The results of the two contemporaneous assays are compared to determine whether a menopausal state exists.

In one embodiment the test results can be interpreted on a qualitative or semi-quantitative basis, for example by eye if the two assays give rise to visible test readings which can be interpreted readily, for example through differences in colour or colour intensity. If necessary this visual determination can be aided by the provision of a reference standard. The two assays can be configured to aid visual assessment.

For more accurate diagnosis of menopausal conditions it may be appropriate for the assay results to be determined numerically. This will usually require a sophisticated reading system, such as by optical transmission or reflectance and which is amenable to measuring small changes in signal intensity and relating these to FSH concentrations. In this situation it may be appropriate to determine the numerical ratio of the signals of the first and second assays. A significant change in this ratio can indicate transition from a pre-menopausal to a post-menopausal state, or vice-versa. Thus the results from a series of contemporaneous tests performed, for example, every few weeks, can be collated and any change in the observed signal ratio used to diagnose a change in condition.

For the purposes of HRT monitoring, the HRT treatment, either in terms of the therapeutic product used or its dose level, can be modulated to maintain the ratio value from successive contemporaneous tests at a pre-determined level, for example.

Test devices using the assays of the invention can be provided for home use or for use in clinics or doctors' offices. Alternatively laboratory-style assays can be used. Preferred assay formats involve the single step format as described, for example, in EP-A-291194. These assays can be used if desired in combination with an electronic reader, for example as described in WO 95/13531. In this instance preferably the electronic reader has an information downloading facility, e.g. by means of a transferable datacard ("smart card"), from which a user, e.g. clinician, can transfer data to a computer during consultation with the patient, in order that stored information from repeated tests can be interpreted properly for diagnostic purposes. The computer can include programmed information that assists the clinician in establishing an appropriate HRT treatment for the individual subject.

Generally, the method of the invention involves the use of one pair of specific binding agents in two contemporaneous assays differing in format.

The following example illustrates aspects of the invention in greater detail.

EXAMPLE

1. Raising Anti-FSH Monoclonal Antibodies

Balb/c mice were immunised with human FSH preparations, derived from urine and pituitary sources, purified by immuno-affinity prior to immunisation. Monoclonal antibodies were produced from the immunised mice using conventional cloning techniques, by fusing spleen cells with SP2/Ag14 cells as the immortal partner.

The subunit specificity of the anti-FSH monoclonal antibodies were assigned by means of anti-alpha subunit antibodies cross reactive with LH, TSH and hCG.

2. Identification of Anti-FSH Antibody Pairs with Fertile State Bias a) A panel of seven human urine samples were used to screen various antibody pairs. The samples from young fertile women (under 35 years of age with regular menstrual cycles) were taken at the (1) early follicular, (2)mid-follicular, (3)ovulation, (4)mid-luteal and (5)late luteal phases of menstrual cycles. For each fertile phase pooled samples from two individuals were used. The phase of the menstrual cycle was determined retrospectively by the urinary profiles of the hormones FSH,LH, E3G and P3G. In addition to the fertile samples, two post menopausal urine samples were used (6) 1 month before commencement of HRT treatment and (7)one taken at least one month after HRT treatment began.

For use in the antibody screen the urine panel was normalised based on FSH concentration estimates. The FSH concentration estimates were obtained using commercially available anti-FSH monoclonal antibodies (Clone No's. 6601 and 6602 from Medix Biochemica, Finland) in a sandwich-format ELISA assay. Samples were normalised by being concentrated using centrifuge filtration.

b) Screening procedure

The following standard buffer solutions were used:
PBSTA:
  Phosphate buffered saline
  0.01M Phosphate pH 7.2
  0.9% Sodium chloride
  0.15% Tween 20
  0.02% Sodium azide
PBSA:
  As above, no Tween 20
PBS: As above, no Tween 20 or sodium azide 1) FSH antibodies for screening were prepared to concentrations of 2.5 μg/ml in 0.2M sodium carbonate buffer pH 8.0.
2) 200 μl of the antibody dilutions were added to wells in High binding Greiner 96-well microtitre plates, which were then incubated overnight at 37° C.
3) The plates were washed three times in PBSTA.
4) 100 μl of 0.38M Tris was added to into all of the plate wells, except the blanking wells to which PBSTA was added. 100 μl of each urine sample from the screening panel (see paragraph a) were added at 15.3 mIU/ml (based on the 6602/6601 assay estimates) to triplicate wells for each antibody/conjugate pairing.

5) The plates were incubated for 1 hour at room temperature.
6) Step 3 was repeated.
7) 200 µl of an optimum dilution in PBSTA of alkaline-phosphatase conjugated anti-beta FSH subunit antibody was added to wells sensitised with anti-alpha FSH subunit capture antibodies. 200 µl of an optimum dilution in PBSTA of alkaline-phosphatase conjugated anti-alpha FSH subunit antibody was added to wells sensitised with anti-beta FSH subunit capture antibodies.
8) As a control in each screening run the urine panel was tested with a reference assay (the "Medix Assay") using Medix Biochemica clone No. 6601 conjugate paired with Medix Biochemica clone No.6602 as the capture antibody.
9) Step 5 was repeated.
10) Step 3 was repeated.
11) 200 µl of DEAE substrate was pipetted into all wells of all plates.
12) Step 5 was repeated.
13) The plates were read on a Dynatech plate reader at 405 nm after 1 hour 30 minutes incubation.
14) The mean value of the triplicates were then calculated, and compared to the Medix assay O.D. values. This allowed antibody pairs showing bias in sample recognition relative to the Medix assay to be identified.

The two hydridoma cell lines referred to earlier, now deposited with the ECACC, were selected using this procedure.

3. Use of Contemporaneous two Step/One Step FSH Assays for Menopause Confirmation The method described in section 4 below was used to test 8 consecutive daily urine samples (around mid-cycle) taken from one fertile woman, and 9 consecutive daily urine samples from one post-menopausal woman.

The FSH concentration in each sample was measured by the two step and one step assays. The ratios obtained are shown in the Table below, and clearly differentiate between fertile and post-menopausal states.

4. Test Methods

Both assays were carried out in a "Delfia" [RTM] Time Resolved Fluoroimmunoassay, supplied by Perkin Elmer Life Sciences, using the standard reagents and buffers as supplied, except where indicated.

a) Two Step Assay
1) FluoroNunc 96-well microtitre plates were sensitised with 200 µl of 5 µg·ml 4813.2 antibody in PBSA coating buffer overnight at 4° C.
2) 4813.2-sensitised plates were washed 2 times with Wash Concentrate (Catalogue No. 1244-114).
3) 200 µl of a blocking buffer was added to each well, and incubated for 1 hour at room temperature with shaking. The blocking buffer was the coating buffer plus 2% BSA.
4) Step 2 was repeated.
5) 50 µl of FSH standard or urine sample and 200 µl Assay Buffer was added per well.
6) Incubated for 6 hours at room temperature with shaking.
7) Wash 3 times with Wash Concentrate.
8) 200 µl of Europium-labelled 4882.1 antibody in Assay Buffer (Catalogue No. 1244-111) added, and incubated for 1 hour at room temperature with shaking. The labelling was conducted using a commercial Europium labelling kit from Perkin Elmer, according to the manufacturer's instructions.
9) Step 7 was repeated.
10) 200 µl Enhancement Solution (Catalogue No. 1244-105) added to each well.
11) Incubation for 5 minutes at room temperature with shaking.
12) Read result.

b) One Step Assay
1) Proceed through steps (1) to (4) of assay (a).
2) Add 200 µl FSH standard or urine sample, and 200 µl Eu-labelled 4882.1 antibody, and incubate for 2 hours at room temperature with shaking.
3) Proceed through steps (9) to (12) of assay (a).

| Individual and Sample Day | Result Ratio of two step to one step Assays |
|---|---|
| Fertile | |
| D14 | 3.5 |
| D15 | 3.8 |
| D16 | 3.8 |
| D17 | 4.0 |
| D18 | 3.8 |
| D19 | 2.9 |
| D20 | 3.4 |
| D21 | 3.1 |
| Post-Menopausal | |
| D10 | 1.2 |
| D11 | 1.3 |
| D12 | 1.2 |
| D13 | 1.8 |
| D14 | 1.3 |
| D16 | 1.3 |
| D17 | 1.3 |
| D18 | 1.3 |
| D19 | 1.5 |

The invention claimed is:

1. A method, comprising:
(a) providing a sample obtained from a human female, the sample comprising an analyte compound which is a member of the gonadotrophin family;
(b) providing a first and a second binding agent, wherein the first binding agent is specific to a first form of the analyte compound characteristic of a menopausal state and the second binding agent is specific to a second form of the analyte compound characteristic of a pre-menopausal or fertile state;
(c) reacting a first portion of the sample with the first binding agent to form a first binding agent/analyte compound complex and subsequently reacting the first binding agent/analyte compound complex with the second binding agent to form a first binding agent/analyte compound/second binding agent complex;
(d) reacting a second portion of the sample substantially simultaneously with the first binding agent and the second binding agent to form a first binding agent/analyte compound/second binding agent complex;
(e) determining the amount of first binding agent/analyte compound/second binding agent/complex formed in step (c) and step (d) and displaying the amounts as a ratio; and
(f) comparing the ratio obtained in step (e) to the ratio obtained from a pre-menopausal control, wherein a difference in the two ratios indicates that the human female is in a post-menopausal state.

2. The method of claim 1, wherein the analyte compound is follicle stimulating hormone.

3. The method according to claim 1, wherein the first and second specific binding agents are antibodies.

4. The method according to claim 3, wherein each binding agent is a monoclonal antibody.

5. The method of claim 1, wherein in the first reacting step, the sample is incubated with a solid phase on which is immobilized the first binding agent, and thereafter, following removal of unbound analyte compound, the solid phase is incubated with the second binding agent.

6. The method of claim 5, wherein in the second reacting step, the sample is substantially simultaneously incubated with a solid phase to which the first binding reagent is immobilized and with the second binding agent in solution or suspension.

7. The method of claim 1, wherein in the second reacting step, the sample is substantially simultaneously incubated with a solid phase to which the first binding reagent is immobilized and with the second binding agent in solution or suspension.

8. The method of claim 1, wherein the first or second binding agent is labeled with a label selected from the group consisting of enzymes, fluorescent labels, radiolabels and direct particulate labels.

9. The method of claim 1, wherein one of the first or second binding agents comprises an anti-FSH antibody expressed by hybridoma cell line ECACC 00032004.

10. The method of claim 1, wherein one of the first or second binding agents comprises an anti-FSH antibody expressed by hybridoma cell line ECACC 00032005.

11. The method of claim 1, wherein one of the first or second binding agents comprises an anti-FSH antibody expressed by hybridoma cell line ECACC 00032004 and the other comprises an anti-FSH antibody expressed by hybridoma cell line ECACC 00032005.

* * * * *